United States Patent
Iwamizu et al.

(10) Patent No.: US 8,348,524 B2
(45) Date of Patent: Jan. 8, 2013

(54) PLUG AND CONNECTING STRUCTURE FOR ENDOSCOPE

(75) Inventors: Keita Iwamizu, Fukuroi (JP); Masatoshi Yokoyama, Fukuroi (JP)

(73) Assignee: Covidien LP, Mansfield, MA (US)

( * ) Notice: Subject to any disclaimer, the term of this patent is extended or adjusted under 35 U.S.C. 154(b) by 304 days.

(21) Appl. No.: 12/651,705

(22) Filed: Jan. 4, 2010

(65) Prior Publication Data

US 2010/0178014 A1 Jul. 15, 2010

(30) Foreign Application Priority Data

Jan. 9, 2009 (JP) ................................. 2009-003417

(51) Int. Cl.
*G02B 6/36* (2006.01)
*G02B 6/06* (2006.01)

(52) U.S. Cl. .......................................... 385/89; 385/117

(58) Field of Classification Search ............... 385/88, 385/89, 135, 147, 53, 58, 65, 70, 77, 117; 600/182

See application file for complete search history.

(56) References Cited

U.S. PATENT DOCUMENTS

| | | | | |
|---|---|---|---|---|
| 4,762,388 A | * | 8/1988 | Tanaka et al. | 385/58 |
| 4,919,621 A | * | 4/1990 | Ams | 439/191 |
| 5,828,804 A | * | 10/1998 | Akins et al. | 385/58 |
| 5,850,496 A | * | 12/1998 | Bellahsene et al. | 385/117 |
| 6,511,230 B1 | * | 1/2003 | Connelly et al. | 385/58 |
| 6,969,348 B2 | * | 11/2005 | Araii | 600/178 |
| 7,018,331 B2 | * | 3/2006 | Chang et al. | 600/182 |
| 7,121,736 B2 | * | 10/2006 | Ayame | 385/81 |
| 2005/0256377 A1 | * | 11/2005 | Deppmeier et al. | 600/176 |
| 2007/0088198 A1 | * | 4/2007 | Koitabashi et al. | 600/136 |

FOREIGN PATENT DOCUMENTS

| | | |
|---|---|---|
| EP | 0156608 A2 | 10/1985 |
| EP | 0837347 A2 | 4/1998 |
| EP | 1001289 A2 | 5/2000 |
| EP | 1122566 A2 | 8/2001 |
| JP | 08304716 A | 11/1996 |

OTHER PUBLICATIONS

European Search Report regarding related application serial No. EP10000020.7, dated Apr. 28, 2010, 6 pages.

* cited by examiner

*Primary Examiner* — Akm Ullah

(57) ABSTRACT

A plug in which the base end portions of an image guide comprise an image guide fiber and an image guide rod. A light guide comprising a light guide fiber and a light guide rod are fixed to a plug main body in a parallel state. The plug and a socket can be connected. The diameter of a position-aligning hole portion into which the base end of the image guide rod is inserted is set to be substantially the same as the outer diameter of the image guide rod, while the diameter of a position-aligning hole portion into which the base end of the light guide rod is inserted is set to be greater than the outer diameter of the light guide rod.

10 Claims, 14 Drawing Sheets

PLUG AND CONNECTING STRUCTURE FOR ENDOSCOPE

FIELD OF THE INVENTION

The present invention generally relates to a plug which is attached to the base end of an endoscope and connected to a socket provided on the main body side of the endoscope device, and to a connecting structure for an endoscope provided with this plug.

BACKGROUND OF THE INVENTION

Optical endoscopes are conventionally used for diagnosis and treatment in patients, for example. These endoscopes house an image guide and a light guide, and the image guide and light guide are connected to a socket which is provided on the main body side of the endoscope device, by way of a plug which is provided at the base end of the endoscope. In this case, if the plug and the socket are not properly connected, the images observed using the endoscope are not clear, and there are fluctuations in the brightness of the illumination provided by the endoscope which make the observed images difficult to see. Consequently, there are also connecting structures provided with packing in order to eliminate rattling between the plug and socket (see Patent Document 1, for example).

This light source device for an endoscope is for electronic endoscopes, and a light guide connector provided with a light guide insertion hole and an electrical contact part provided with an electrical contact are arranged in a line in a connector receiver (socket) of the light source device for an endoscope. The entry portion of the electrical contact part is then provided with a U-shaped frame, and packing made of rubber which is elastic is joined to the inner peripheral surface of this frame. Furthermore, a light guide incident end which is inserted into the light guide insertion hole and an electrical contact which is connected to the electrical contact of the connector receiver are arranged in a line on a light guide connector (plug) of the endoscope. Consequently, the light guide connector can be connected to the connector receiver in a state in which rattling is prevented by means of the packing.

SUMMARY OF THE INVENTION

However, with the conventional light source device for an endoscope described above, although it is possible to prevent rattling between the connector receiver and the light guide connector to a certain extent, the connector receiver and the light guide connector require a separate frame and packing. Consequently, there are more components with conventional light source devices for endoscopes, which makes the structure more complex.

Furthermore, if use is made of an endoscope device provided with an optical endoscope, and the base ends of the image guide and light guide of the endoscope are arranged inside the same connector, and the connector receiver for the image guide and the connector receiver for the light guide on the endoscope device side comprise the same connector receiver, it is difficult to accurately align the positions of both the image guide and light guide in the connection terminals of the connector receiver when the connector has been inserted into the connector receiver.

The present invention has been devised in view of the situation outlined above, and it aims to provide a plug which makes it possible to fix the ends of an image guide and a light guide in the same plug to facilitate attachment and detachment operations, and to provide a connecting structure for an endoscope which is provided with the plug and makes it possible to accurately position the image guide in the socket.

In order to achieve the abovementioned aim, the plug according to the present invention is attached to the base end of an endoscope and connected to a socket provided on the main body side of the endoscope device, said plug consisting of: an image guide comprising an image guide fiber and an image guide rod for covering the base end of the image guide fiber; a light guide comprising a light guide fiber and a light guide rod for covering the base end of the light guide fiber; and a plug main body in which the base end portions of the image guide and the light guide are fixed in a parallel state with a space between them.

With the plug according to the present invention, the base end of the image guide fiber is covered by the image guide rod to configure the image guide, while the base end of the light guide fiber is covered by a light guide rod to configure the light guide. The base end portions of the light guide and the image guide are then fixed in the plug main body in a parallel state with a space between them to configure the plug. Consequently, both the image guide and the light guide can be connected to the main body of the endoscope device and the connection thereof released by an operation to connect the plug to the socket or withdraw it from the socket, which is a simple operation.

Other structural features of the present invention lie in the fact that the plug main body consists of a rod fixing part for fixing the image guide rod and the light guide rod, and a fiber housing part for housing the image guide fiber and the light guide fiber. In this case, the rod fixing part and fiber housing part preferably comprise separate members, and the plug main body is preferably configured by assembling the rod fixing part and fiber housing part which are separate members. This means that the plug main body can be simply produced, and the operation to attach the image guide and light guide to the plug main body is simplified.

Further structural features of the present invention lie in the fact that the outer diameter of the light guide rod and the outer diameter of the image guide rod are set to be different. This means that, if, for example, the respective inner diameters of the connecting portions of the socket corresponding to the light guide rod and image guide rod are the same, the outer diameter of the one out of the light guide rod and image guide rod for which less connection precision is required can be made smaller than the outer diameter of the one for which greater connection precision is required. Consequently, the image guide or light guide for which connection precision is required can be properly connected to the socket. In this case, the outer diameters which fit with the inner diameters of the parts of the connecting portion of the socket corresponding to each are preferably such that the outer diameter of the light guide is smaller than the outer diameter of the image guide.

Structural features of the connecting structure for an endoscope according to the present invention lie in the fact that any one of the plugs described above is connected to the socket, and the socket is provided with two insertion holes into which the image guide and the light guide are respectively inserted, and a portion of the two insertion holes opposite the plug consists of an introduction fitting hole for receiving the light guide and the image guide, and a portion of the two insertion holes on the main body side of the endoscope device consists of a position-aligning hole for regulating the position of the light guide and the image guide.

With the connecting structure for an endoscope according to the present invention, the two insertion holes into which the light guide and the image guide are inserted, which holes are provided in the socket into which the plug is inserted, comprise an introduction fitting hole on the open side opposite the plug, and comprise a position-aligning hole for regulating the position of the light guide and the image guide on the main body side of the endoscope device, on the inside. Consequently, when the light guide and the image guide are inserted into the corresponding insertion holes, the base ends of the light guide and image guide enter the position-aligning holes while being guided by means of the fitting holes, and they are regulated so as to be correctly positioned by means of the position-aligning holes.

Further structural features of the connecting structure for an endoscope according to the present invention lie in the fact that the difference between the outer diameter of the image guide and the inner diameter of the position-aligning hole into which the image guide is inserted, and the difference between the outer diameter of the light guide and the inner diameter of the position-aligning hole into which the light guide is inserted are set to be different. This means that by making the inner diameter of the position-aligning hole for the image guide or light guide for which greater connection precision is required, out of the two insertion holes, substantially the same as the outer diameter of the image guide or light guide which is inserted, and by making the inner diameter of the position-aligning hole for which less connection precision is required somewhat greater than the outer diameter of the light guide or image guide which is inserted, it is possible to leave some space. Consequently, the image guide or light guide for which connection precision is required can be properly connected to the socket. In this case, the difference between the outer diameter of the light guide and the inner diameter of the position-aligning hole into which the light guide is inserted is preferably greater than the difference between the outer diameter of the image guide and the inner diameter of the position-aligning hole into which the image guide is inserted.

Further structural features of the connecting structure for an endoscope according to the present invention lie in the fact that the inner diameter of the fitting hole is set to decrease moving towards the position-aligning hole from the open side opposite the plug, and the inner diameter of the position-aligning hole is set to be the same as the inner diameter at the end of the fitting hole on the position-aligning hole side. This means that the base ends of the image guide and light guide enter the position-aligning holes while being guided by means of the fitting holes so as to be positioned in the centre of the insertion holes, and they are regulated so as to be correctly positioned by means of the position-aligning holes. It is also possible to prevent the plug from rattling in the socket.

Further structural features of the connecting structure for an endoscope according to the present invention lie in the fact that the plug is provided with an elastic engaging piece whereof the base end consists of an engaging part which is linked to the base end of the plug main body, and the tip end consists of a pressing part of smaller width than the engaging part which is formed so as to be separated from the plug main body, while the socket is provided with an engaging wall part having a hole to be engaged which consists of a wide hole having a width which allows the insertion of the engaging part and a narrow hole which connects to the wide hole and has a width allowing the insertion of the pressing part; when the plug is fitted into the socket, the engaging part is pressed at the edge of the wide hole so as to be urged towards the plug main body, and when the engaging part has passed through the wide hole, it is moved away from the plug main body so that the pressing part is positioned inside the narrow hole, and the engaging part engages with the edge of the narrow hole.

This means that when the plug is inserted into the socket, the engaging part is pressed at the edge of the wide hole so as to be urged towards the plug main body, and when the engaging part has passed through the wide hole, it is moved away from the plug main body so as to engage with the edge of the narrow hole. At this point, the pressing part is positioned inside the narrow hole. By means of this, the linked state of the plug and socket can be maintained. Furthermore, by pulling the plug out of the socket with the pressing part urged towards the plug main body, the plug can be easily withdrawn from the socket. This means that the plug and the socket can be stably connected.

Other objects and features will be in part apparent and in part pointed out hereinafter.

REFERENCE CHARACTERS

10—connecting structure for an endoscope;
11—fiber shaft;
12—image guide fiber;
13—light guide fiber;
14—image guide rod;
15—light guide rod;
20—plug;
20*a*—plug main body;

21—plug handle;
23—plug male end;
26—elastic engaging piece;
26a—engaging part;
26b—pressing part;
30—socket;
32a,32b—position-aligning hole;
36—engaging wall part;
36a—wide hole;
36b—narrow hole; and
37a,37b—fitting hole.

DESCRIPTION OF THE PREFERRED EMBODIMENTS

Figure 1:
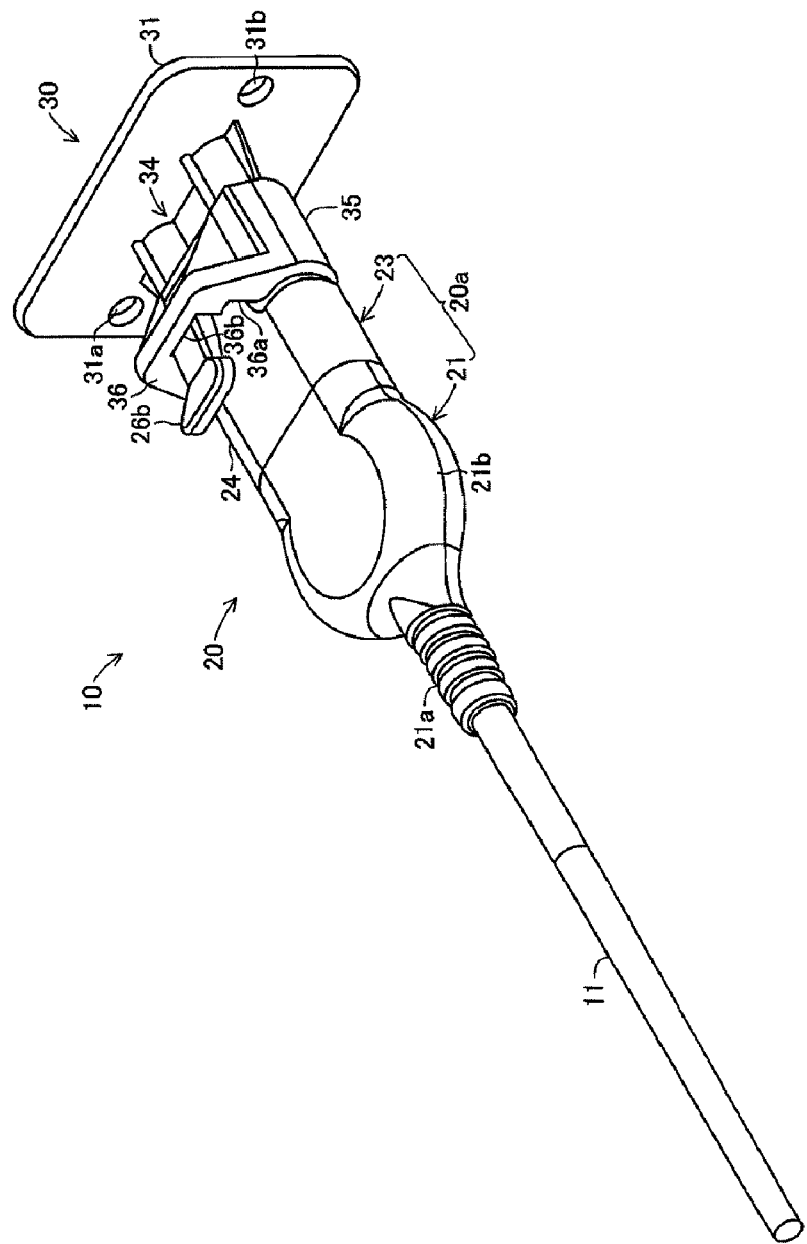
FIG. 1 is an oblique view showing the connected state of the connecting structure for an endoscope according to a mode of embodiment of the present invention.
Figure 2:
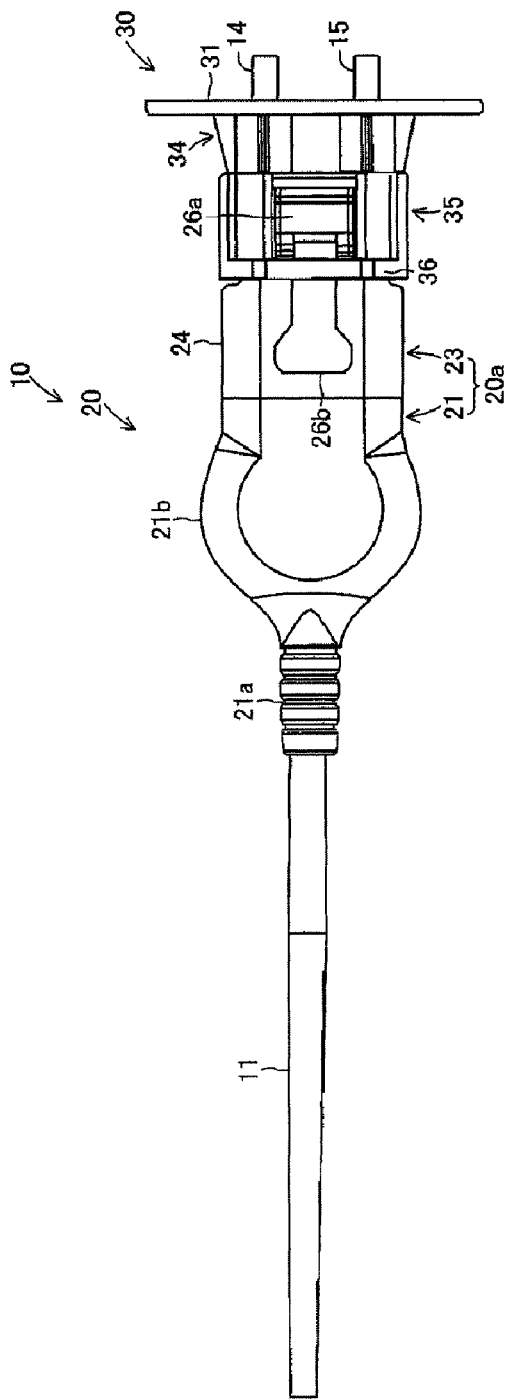
FIG. 2 is a plan view of the connecting structure for an endoscope.
Figure 3:
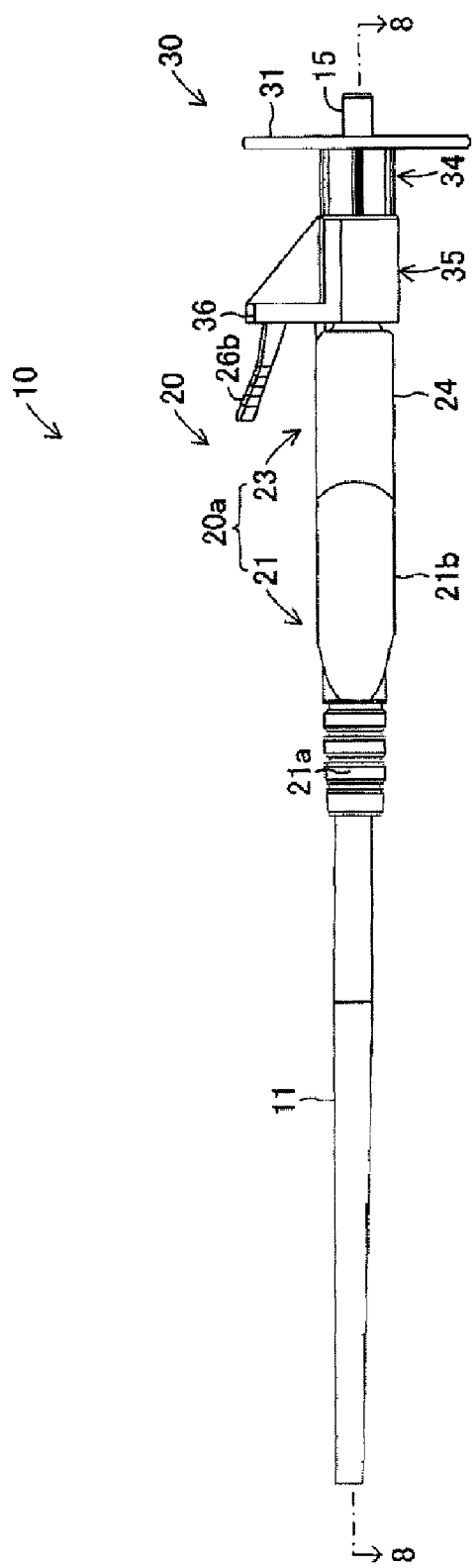
FIG. 3 is a front view of the connecting structure for an endoscope.
Figure 4:
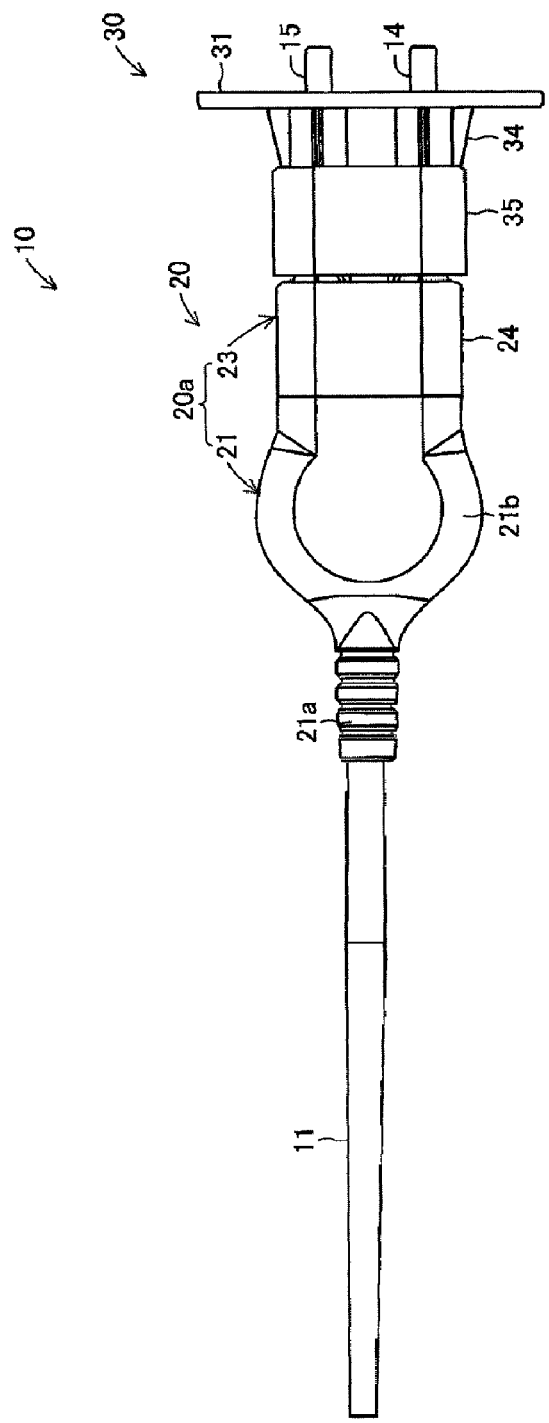
FIG. 4 is a bottom view of the connecting structure for an endoscope.
Figure 5:
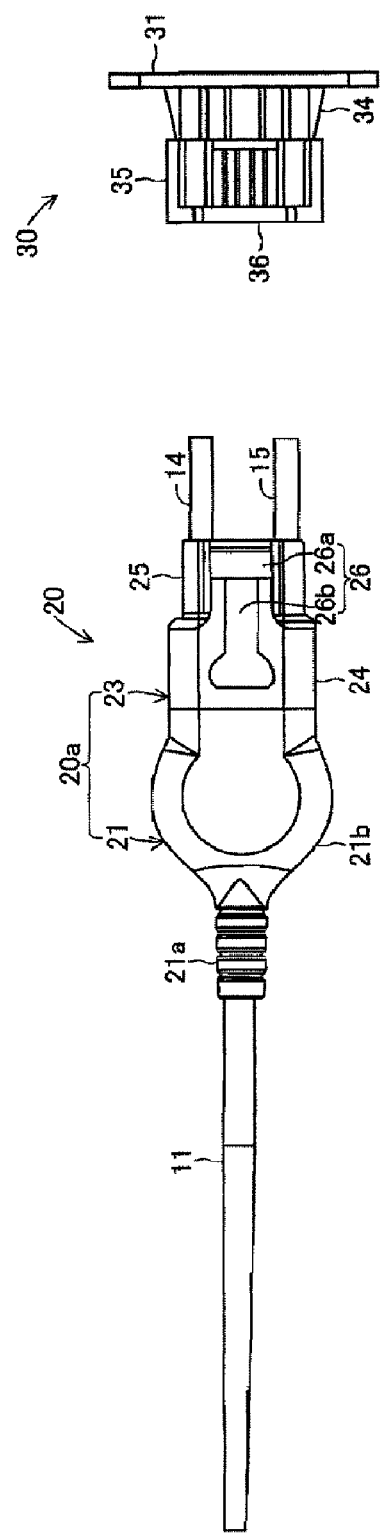
FIG. 5 is a plan view showing a state in which the connection of the connecting structure for an endoscope has been released.
Figure 6:
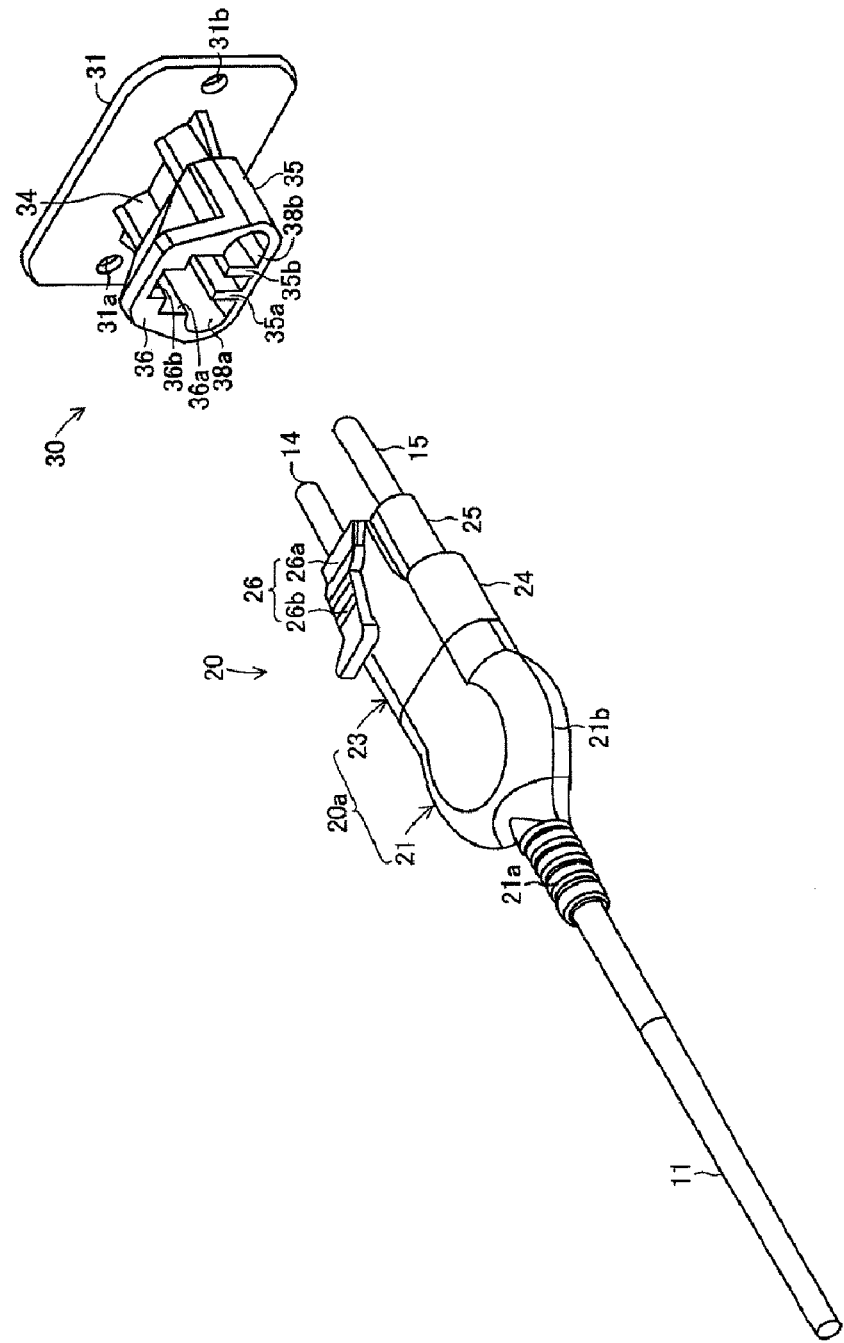
FIG. 6 is an oblique view showing a state in which the connection of the connecting structure for an endoscope has been released, seen obliquely from above.
Figure 7:
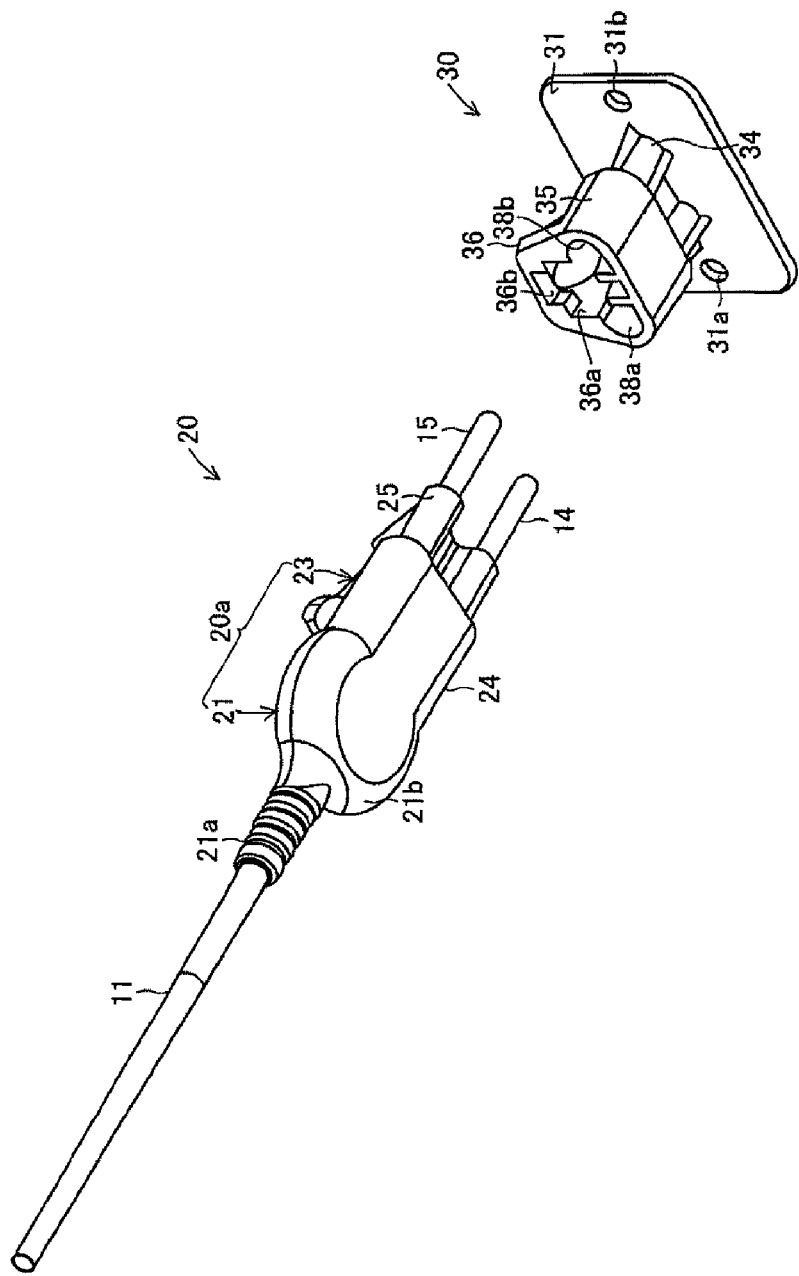
FIG. 7 is an oblique view showing a state in which the connection of the connecting structure for an endoscope has been released, seen obliquely from below.

A detailed description will be given below of the connecting structure for an endoscope provided with a plug, according to a mode of embodiment of the present invention, with the aid of the figures. FIGS. 1 to 7 show a connecting structure 10 for an endoscope, in accordance with this mode of embodiment. This connecting structure 10 for an endoscope consists of a plug 20 which configures the base end portion of a fiber shaft 11 of an endoscope which is inserted into a patient's stomach or intestines etc. to observe the inside of the stomach or intestines, and a socket 30 which is arranged on the main body side (not depicted) of the endoscope device to which the plug 20 is connected. FIGS. 1 to 4 show a state in which the plug 20 and socket 30 are connected, and FIGS. 5 to 7 show a state in which the connection of the plug 20 and socket 30 has been released. Furthermore, in order to simplify the following description, the direction towards the tip end of the endoscope shall be referred to as the tip end or front or forwards, the direction where the main body of the endoscope device is positioned shall be referred to as the base end or rear or rearwards, and the vertical direction shall refer to the vertical direction in FIG. 1.

Figure 8:
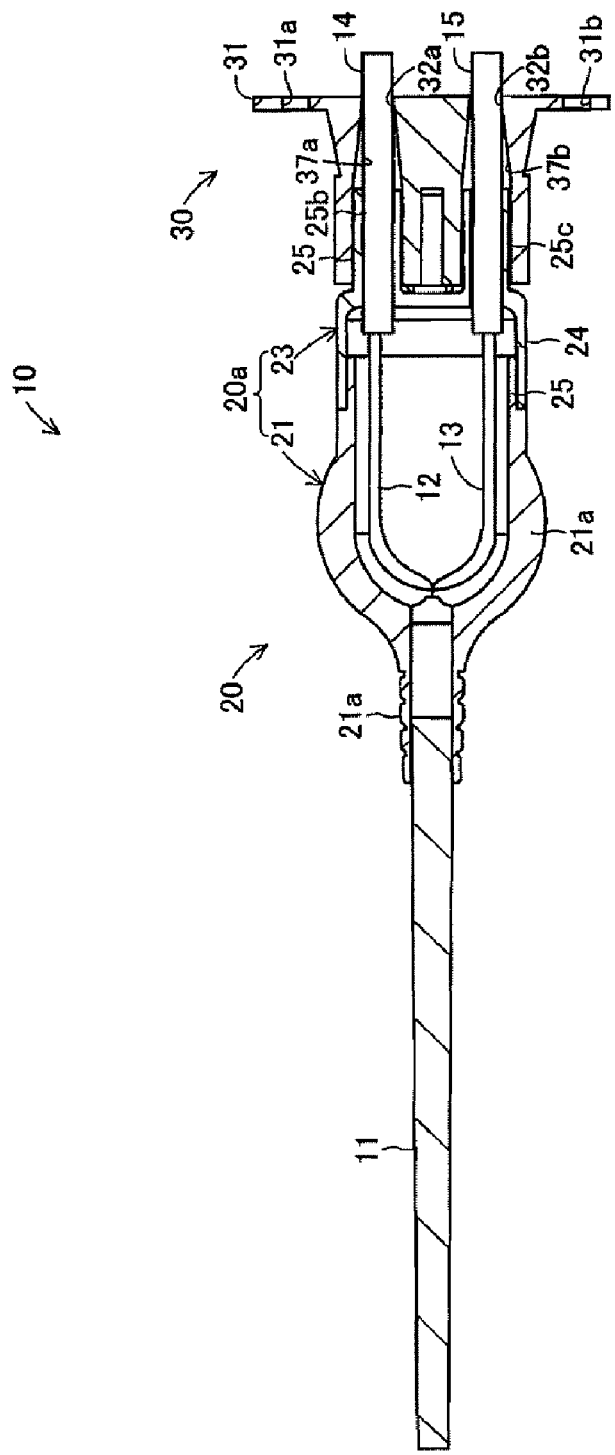
FIG. 8 is a view in cross section along 8-8 in FIG. 3.
Figure 9:
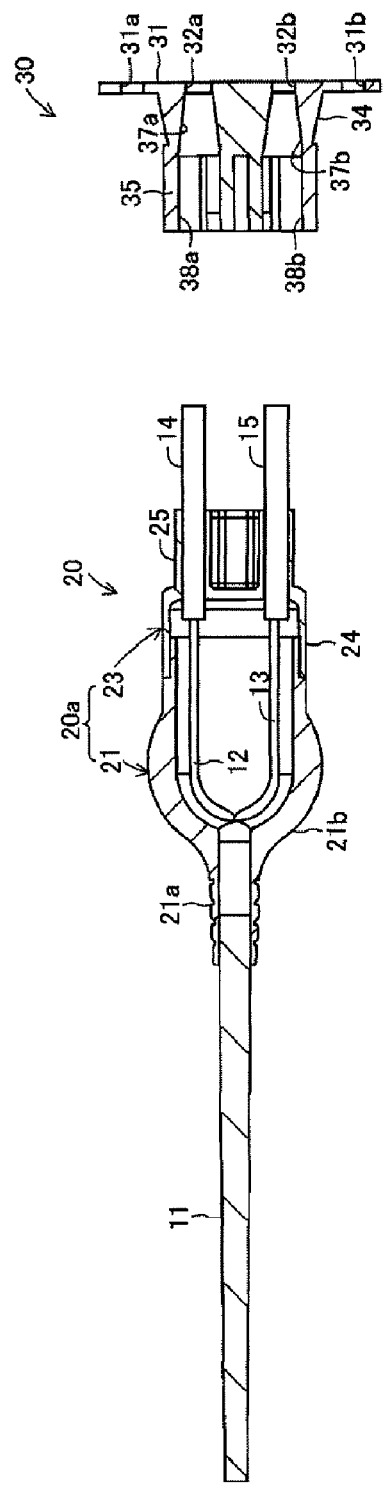
FIG. 9 is a view in cross section of the connecting structure for an endoscope shown in FIG. 5.

A plug main body 20a which defines the outline of the plug 20 consists of a plug handle 21 which acts as the fiber housing part according to the present invention which is linked to the base end of the fiber shaft 11, and a plug male end 23 which acts as the rod fixing part according to the present invention which is linked to the rear of the plug handle 21. An image guide fiber 12 and a light guide fiber 13 (see FIGS. 8 and 9) are bundled and housed inside the fiber shaft 11. The base end portions of the image guide fiber 12 and light guide fiber 13 are then separated at the base end of the fiber shaft 11 and housed inside the plug handle 21, as shown in FIGS. 8 and 9.

Figure 10:
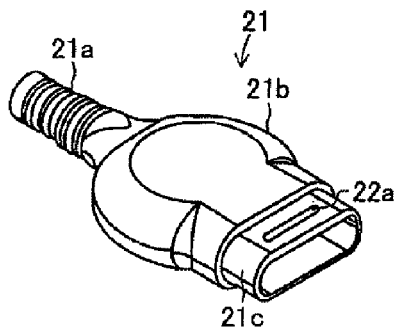
FIG. 10 is an oblique view of the plug handle.
Figure 11:
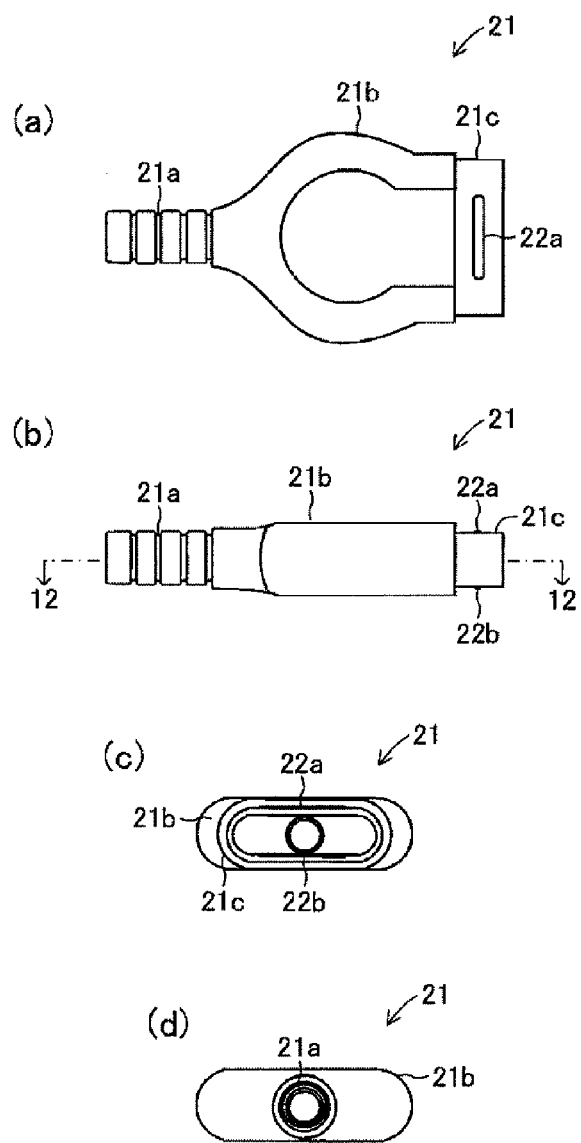
FIG. 11 shows the plug handle, where (a) is a plan view, (b) is a front view, (c) is a side view from the right-hand side, and (d) is a side view from the left-hand side.
Figure 12:
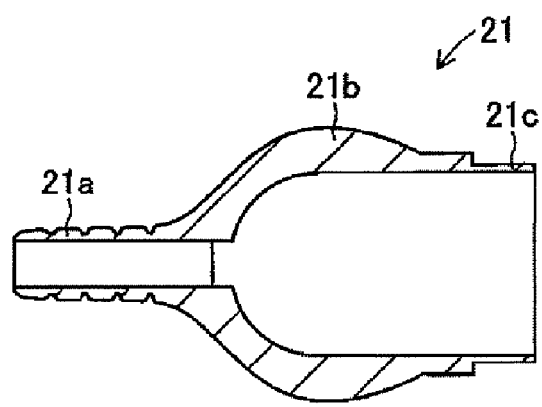
FIG. 12 is a view in cross section along 12-12 in FIG. 11(*b*)

That is to say, the plug handle 21 is configured in the manner shown in FIGS. 10 and 11, consisting of a cylindrical fixing part 21a which is fixed to the outer periphery at the base end of the fiber shaft 11, a flat housing part 21b which is linked to the base end of the fixing part 21a, and an insertion part 21c which projects rearwards from the base end of the housing part 21b. As shown in FIG. 12, the end on the fixing part 21a side is semicircular, and the portion running from the centre to the base end is square, forming a housing space which is open at the base end. The base end portions of the image guide fiber 12 and light guide fiber 13 separate so as to describe a U-shape along both sides on the inner peripheral surface of the housing part 21b, after which they extend towards the base end of the insertion part 21c.

Furthermore, the outer periphery of the insertion part 21c is formed to be slightly narrower overall than the outer periphery of the open portion of the housing part 21b, and a step is provided between the outer peripheral surface of the housing part 21b and the outer peripheral surface of the insertion part 21c. Elongate engaging projections 22a, 22b which extend in the width direction of the insertion part 21c are then formed on both the flat upper and lower surfaces of the insertion part 21c. Furthermore, the base end portion of the image guide fiber 12 is covered by a cylindrical image guide rod 14, and the base end portion of the light guide fiber 13 is covered by a cylindrical light guide rod 15.

Figure 13:
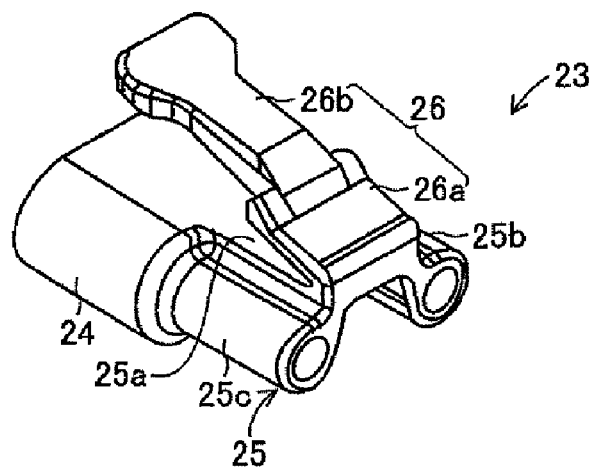
FIG. 13 is an oblique view of the plug male end.
Figure 14:
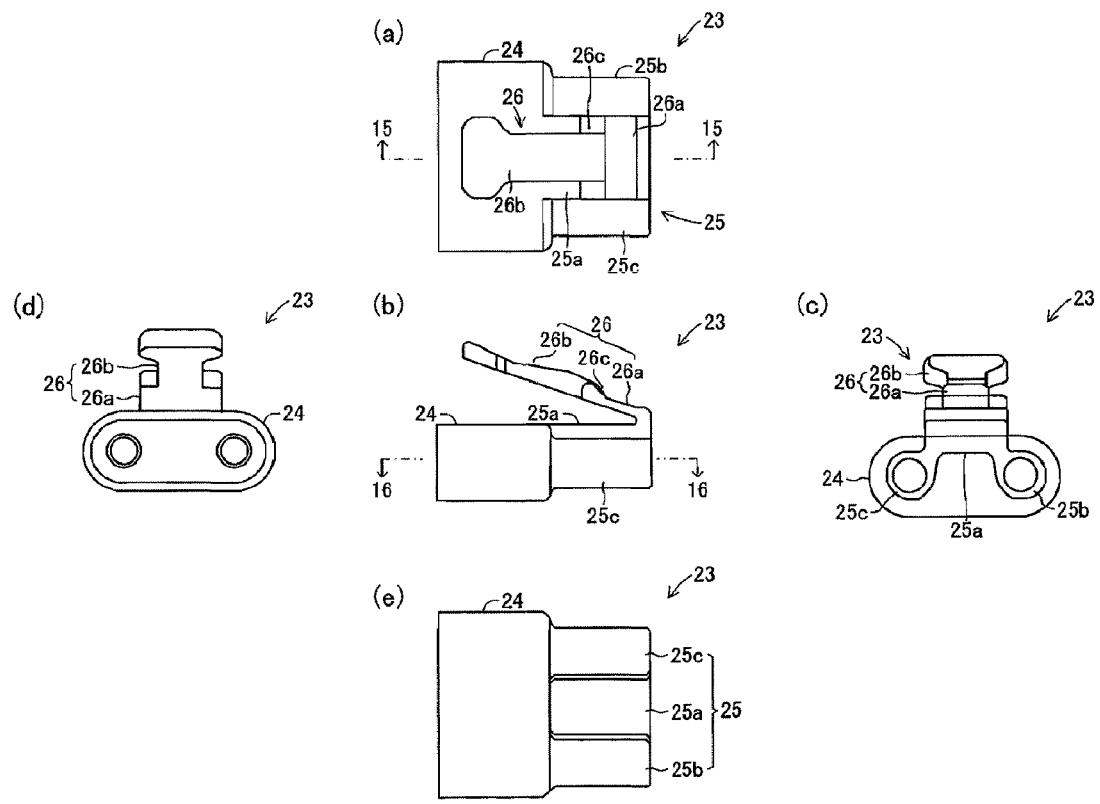
FIG. 14 shows the plug male end, where (a) is a plan view, (b) is a front view, (c) is a side view from the right-hand side, (d) is a side view from the left-hand side, and (e) is a bottom view.

Moreover, the image guide according to the present invention is made up of the base end portion of the image guide fiber 12 and the image guide rod 14, and the light guide according to the present invention is made up of the base end portion of the light guide fiber 13 and the light guide rod 15. The image guide rod 14 and the light guide rod 15 are then fixed to the plug male end 23. The plug male end 23 is configured in the manner shown in FIGS. 13 and 14, consisting of a covering linking part 24 which is linked to the insertion part 21c in a state in which it covers the insertion part 21c of the plug handle 21, a rod insertion part 25 which projects rearwards from the rear of the covering linking part 24, and an elastic engaging piece 26 which is linked to the rod insertion part 25.

Figure 15:
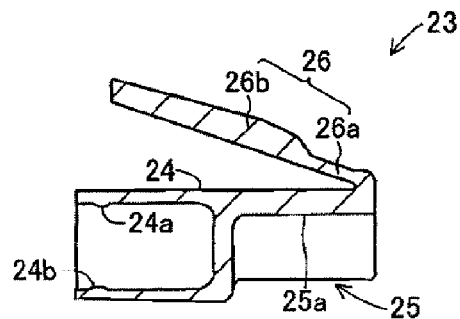
FIG. 15 is a view in cross section along 15-15 in FIG. 14(*a*)
Figure 16:
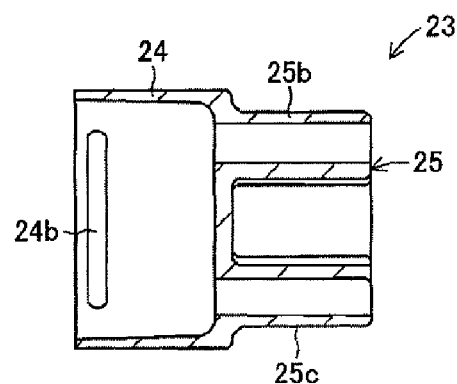
FIG. 16 is a view in cross section along 16-16 in FIG. 14(*b*)

The covering linking part 24 is formed with a flat cylindrical shape with which the insertion part 21 can fit together, and as shown in FIGS. 15 and 16, an engaging projection 24a which can engage with the engaging projection 22a, and an engaging projection 24b which can engage with the engaging projection 22b are formed opposite one another. The rod insertion part 25 consists of a linking plate 25a which extends rearwards from the flat upper surface of the covering linking part 24, and a pair of cylindrical fixing parts 25b, 25c which are arranged in parallel at the lower part on both sides of the linking plate 25a. The upper surface of the linking plate 25a lies on the same surface as the upper surface of the covering linking part 24 and it extends rearwards from the base end of the covering linking part 24; the width thereof is somewhat less than the width of the flat portion on the upper surface of the covering linking part 24.

The cylindrical fixing parts 25b, 25c both have a cylindrical shape with a hole that communicates with the internal space of the covering linking part 24, the cylindrical fixing part 25b fixedly positioning the image guide rod 14 in the internal hole, and the cylindrical fixing part 25c fixedly positioning the light guide rod 15 in the internal hole. Moreover, the inner diameter of the hole in the cylindrical fixing part 25b is set at 2.03 mm, while the inner diameter of the hole in the cylindrical fixing part 25c is set at 2.16 mm. To match these, the outer diameter of the image guide rod 14 is set at approximately 2.00 mm, while the outer diameter of the light guide rod 15 is set at approximately 2.13 mm.

The elastic engaging piece 26 comprises an elastic piece which extends obliquely upwards and forwards from the upper surface at the base end of the linking plate 25a, and it consists of an engaging part 26a which is linked by a hinge to the linking plate 25a, and a pressing part 26b which extends forwards from the tip end of the engaging part 26a. The engaging part 26a has a substantially square plate shape, and a tapered part 26c which becomes thicker towards the front is formed on the upper surface at the front. Furthermore, the pressing part 26b is formed as a narrower and longer plate shape than the engaging part 26a, and it extends forwards from the centre in the width direction of the tapered part 26c. The base end of the pressing part 26b is arranged so as to overlap the tapered part 26c, and a tapered surface at a somewhat greater angle than the angle of the tapered part 26c is formed on the upper surface of the base end of the pressing part 26b.

The insertion part 21c is inserted into the covering linking part 24 of the plug male end 23 which is configured in this manner, and the engaging projections 24a, 24b engage with the engaging projections 22a, 22b and are bonded by an epoxy-based adhesive, whereby said plug male end is assembled with the plug handle 21, configuring the plug main body 20a. Furthermore, the base end portions of the image guide fiber 12 and light guide fiber 13 are separated inside the plug handle 21 and extend rearwards, and the image guide rod 14 which covers the base end of the image guide fiber 12 and the light guide rod 15 which covers the base end of the light guide fiber 13 are fixed in parallel in the plug male end 23. The base ends of the image guide rod 14 and the light guide rod 15 project by the same length of projection from the plug main body 20a (rod insertion part 25).

Figure 17:
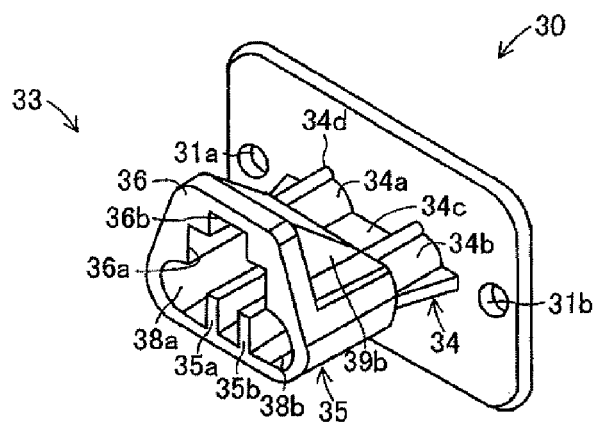
FIG. 17 is an oblique view of the socket.
Figure 18:
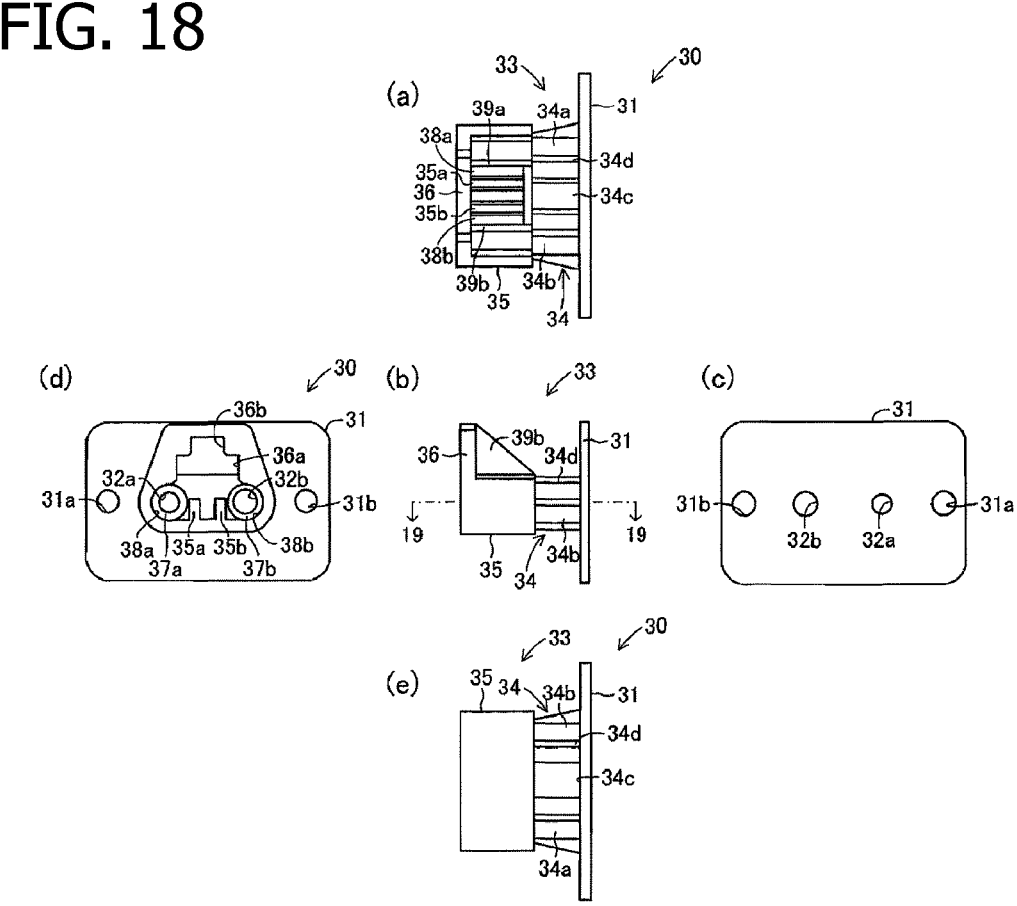
FIG. 18 shows the socket, where (a) is a plan view, (b) is a front view, (c) is a side view from the right-hand side, (d) is a side view from the left-hand side, and (e) is a bottom view.

The socket 30 is a member for connecting the image guide fiber 12 and light guide fiber 13 of the endoscope to the main body of the endoscope device, with the plug main body 20a interposed, and as shown in FIGS. 17 and 18, it consists of a fixing plate 31 which is fixed to the main body of the endoscope device, and a plug female end 33 which projects forwards from the front surface of the fixing plate 31. The fixing plate 31 is formed as a square plate shape which is somewhat longer in the lateral direction than the vertical direction, and insertion holes 31a, 31b for the insertion of fixing screws are formed on both lateral sides in substantially the vertical centre, a pair of position-aligning holes 32a, 32b being formed with a space between them between the insertion holes 31a, 31b.

The space between the centers of the position-aligning holes 32a, 32b is set to be the same as the space between the centers of the cylindrical fixing parts 25b, 25c of the plug 20, and the base end of the image guide is inserted into the position-aligning hole 32a, the base end of the light guide being inserted into the position-aligning hole 32b. Moreover, the diameter of the position-aligning hole 32a is set at 2.03 mm and the diameter of the position-aligning hole 32b is set at 2.4 mm. That is to say, the diameter of the position-aligning hole 32a is set to be the same as the inner diameter of the hole in the cylindrical fixing part 25b, and the diameter of the position-aligning hole 32b is set to be greater than the inner diameter of the hole in the cylindrical fixing part 25c.

Figure 19:
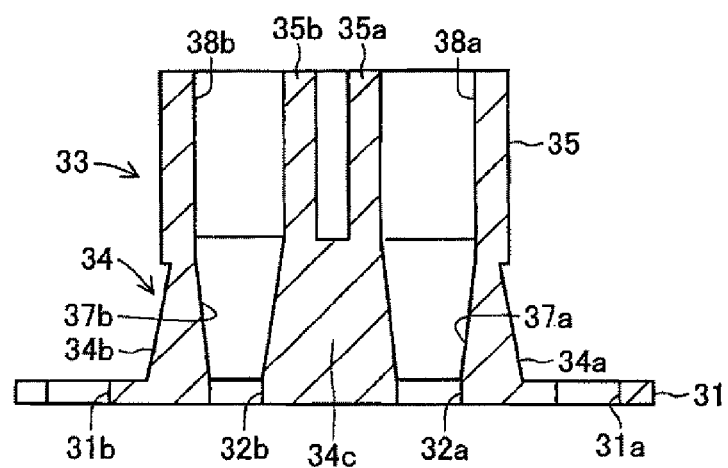
FIG. 19 is a view in cross section along 19-19 in FIG. 18(*b*).

The plug female end 33 is provided with a fitting part 34 which extends forwards from the front surface of the fixing plate 31, a guide part 35 which extends forwards from the front part of the fitting part 34, and an engaging wall part 36 which is formed at the upper part on the front end of the guide part 35. The fitting part 34 has a configuration in which a pair of cylindrical insertion parts 34a, 34b are linked by a plate-like linking part 34c, and as shown in FIG. 19, tapered fitting holes 37a, 37b having a diameter which grows steadily smaller moving rearwards from the front are formed inside the cylindrical insertion parts 34a, 34b.

The diameter of the rear end of the fitting hole 37a is the same size as the diameter of the position-aligning hole 32a, and the fitting hole 37a and the position-aligning hole 32a communicate. Furthermore, the diameter of the rear end of the fitting hole 37b is the same size as the diameter of the position-aligning hole 32b, and the fitting hole 37b and the position-aligning hole 32b communicate. A number of reinforcing ribs 34d are then provided at intervals of 90° in the peripheral direction on a portion of the outer peripheral surface of the cylindrical insertion parts 34a, 34b other than the portions where the linking part 34c joins them.

The guide part 35 is formed with an open shape in which the flat part on the upper surface of a flat cylindrical body the same shape as the covering linking part 24 of the plug male end 23 has been removed, and open guide holes 38a, 38b which are open in the centre are formed on both lateral sides on the inner peripheral surface. A pair of guide walls 35a, 35b are then formed on the inside of the open guide holes 38a, 38b. The open guide holes 38a, 38b consist of groove-like holes of which the outside portion in longitudinal section is a semicircular arc, and the inside portion is open.

The guide wall 35a extends the upper surface at the bottom part of the guide part 35 in the front to rear direction, with a space that allows the cylindrical fixing part 25b of the plug male end 23 to be inserted between said wall and the open guide hole 38a; the guide wall 35b extends the upper surface at the bottom part of the guide part 35 in the front to rear direction, with a space that allows the cylindrical fixing part 25c of the plug male end 23 to be inserted between said wall and the open guide hole 38b. By means of this, as shown in FIG. 19, a single continuous insertion hole comprising a hole constituted by the open guide hole 38a and guide wall 35a, the fitting hole 37a and the position-aligning hole 32a, and a single continuous insertion hole comprising a hole constituted by the open guide hole 38b and guide wall 35b, the fitting hole 37b and the position-aligning hole 32b, are formed at the plug female end 33.

The engaging wall part 36 consists of a wall part with a substantially trapezoidal frame shape which is formed at the upper part at the front end of the guide part 35, and a hole to be engaged comprising a wide hole 36a which communicates with an opening in the guide part 35 and a narrow hole 36b which is provided at the upper part of the wide hole 36a, is formed on the inner periphery thereof. The wide hole 36a is wide enough for the engaging part 26a of the elastic engaging piece 26 to pass through, and the narrow hole 36b is wide enough for the pressing part 26b of the elastic engaging piece 26 to pass through. Furthermore, the wide hole 36a is high enough for the engaging part 26a to pass through when the rod insertion part 25 of the plug male end 23 has been inserted into the guide part 35 of the plug female end 33 in a state in which the engaging part 26a is urged towards the plug male end 23.

Consequently, when the plug male end 23 is inserted into the plug female end 33, the tapered part 26c of the elastic engaging piece 26 comes into contact with the edge of the wide hole 36a on both sides at the upper part, so that the elastic engaging piece 26 is urged towards the plug male end 23. Then, when the engaging part 26a passes through the wide hole 36a, the elastic engaging piece 26 is moved away from the plug male end 33 by the elastic force of the elastic engaging piece 26. Consequently, the pressing part 26b enters the narrow hole 36b, and both sides of the engaging part 26a at the front end engage with both edges of the narrow hole 36b, and the connected state of the plug male end 23 and plug female end 33 is maintained.

At this point, the rod insertion part 25 of the plug male end 23 is positioned inside the guide part 35 of the plug female end 33. The image guide then enters the position-aligning hole 32a from the fitting hole 37a, and the light guide enters the position-aligning hole 32b from the fitting hole 37b. Furthermore, when the state of connection of the plug male end 23 and the plug female end 33 is released, the pressing part 26b is pressed towards the plug male end 23, and the plug male end 23 is pulled from the plug female end 33. Furthermore, reinforcing ribs 39a, 39b are formed between the rear surface of the engaging wall part 36 and the edge at the upper surface opening of the guide part 35.

With this configuration, when the plug 20 is connected to the socket 30, the plug 20 is moved closer to the socket 30 from the state shown in FIGS. 5 to 7. By means of this, the image guide rod 14 enters the hole which comprises the open guide hole 38a and guide wall 35a of the plug female end 33 and the light guide rod 15 enters the hole comprising the open guide hole 38b and guide wall 35b of the plug female end 33. In addition, when the plug 20 is moved closer to the socket 30, the image guide rod 14 enters the position-aligning hole 32a from the fitting hole 37a, and the light guide rod 15 enters the position-aligning hole 32b from the fitting hole 37b.

At this point, the outer diameter of the image guide rod 14 is substantially the same as the diameter of the position-aligning hole 32a, and therefore the image guide rod 14 enters the position-aligning hole 32a in a state in which the axis thereof is aligned with the centre of the position-aligning hole 32a. On the other hand, the outer diameter of the light guide rod 15 is smaller than the diameter of the position-aligning hole 32b, and therefore the light guide rod 15 enters the position-aligning hole 32b in a state in which there is a certain amount of space. As a result, the light guide rod 15 is inserted into the position-aligning hole 32b, whereby it is possible to prevent unnecessary force being applied to the image guide rod 14, and clear observation images are displayed on the display apparatus with which the endoscope device is provided.

Furthermore, while the image guide rod 14 and light guide rod 15 are being inserted into the socket 30, the rod insertion part 25 fits into the guide part 35, and the elastic engaging piece 26 engages with the engaging wall part 36. By means of this, the plug 20 is maintained in the socket 30 in a stable state of connection. Moreover, the light guide does not require as much connection precision as the image guide with respect to the connection terminals on the socket 30 side, and therefore the endoscope can be supplied with the correct degree of illuminating light even if the axis of the base end of the light guide is not completely aligned with the centre of the position-aligning hole 32b.

In this way, with the plug 20 and the connecting structure 10 for an endoscope which is provided with the plug 20, in accordance with this mode of embodiment, the base end portions of the image guide and the light guide are fixed to the plug main body 20a in a parallel state with a constant space between them. Consequently, both the image guide and the light guide can be connected to the main body of the endoscope device and the connection thereof released by a single operation to connect the plug 20 to the socket 30 or withdraw it from the socket, which is a simple operation. Furthermore, the plug main body 20a consists of an assembly comprising separate members, namely the plug handle 21 which houses the image guide fiber 12 and light guide fiber 13, and the plug male end 23 which fixes the image guide rod 14 and light guide rod 15. Consequently, the structure of the plug main body 20a is simplified, while the operation to attach the image guide and light guide to the plug main body 20a is also simplified.

Furthermore, the outer diameter of the light guide rod 15 is greater than the outer diameter of the image guide rod 14, and the diameter of the position-aligning hole 32a is substantially the same as the outer diameter of the image guide rod 14, and the diameter of the position-aligning hole 32b is greater than the outer diameter of the light guide rod 15. Consequently, the image guide which requires connection precision can be properly connected to the socket 30. In addition, the base end parts of the image guide rod 14 and light guide rod 15 are made to project by the same length from the plug main body 20a, and therefore when the plug 20 is inserted into the socket 30, the base end of the image guide and the base end of the light guide make contact with the connection terminals on the socket 30 side at the same time.

Furthermore, in this mode of embodiment, the two insertion holes provided in the socket 30 consist of one insertion hole comprising a hole constituted by the open guide hole 38a and guide wall 35a, the fitting hole 37a and the position-aligning hole 32a, and another insertion hole comprising a hole constituted by the open guide hole 38b and guide wall 35b, the fitting hole 37b and the position-aligning hole 32b. The fitting hole 37a into which the image guide is inserted and the fitting hole 37b into which the light guide is inserted are formed so that the diameter thereof becomes smaller moving towards the position-aligning holes 32a, 32b from the open side opposite the plug 20.

Consequently, the base end of the image guide enters the position-aligning hole 32a while being guided by means of the fitting hole 37a so as to be positioned at the centre of the insertion hole, and the correct position thereof is regulated by the position-aligning hole 32a. Furthermore, the base end of the light guide enters the position-aligning hole 32b while being guided by means of the fitting hole 37b so as to be positioned at the centre of the insertion hole, and it is positioned in the correct place with a certain amount of space by means of the position-aligning hole 32b. Furthermore, with the connecting structure 10 for an endoscope in accordance with this mode of embodiment, the plug 20 is provided with the elastic engaging piece 26 which consists of the engaging part 26a and the pressing part 26b, while the socket 30 is provided with the engaging wall part 36 which has a hole to be engaged consisting of the wide hole 36a into which the engaging part 26a can be inserted, and the narrow hole 36b which is linked to the wide hole 36a and into which the pressing part 26b can be inserted.

Then, when the socket 30 is inserted into the plug 20, the engaging part 26a is pressed at the edge of the wide hole 36a so as to be urged towards the plug main body 20a, and when the engaging part 26a has passed through the wide hole 36a, it is moved away from the plug main body 20a so that the pressing part 26b is positioned inside the narrow hole 36b, and the engaging part 26a engages with the edge of the narrow hole 36b. Furthermore, when the connected state of the plug 20 and socket 30 is released, the plug 20 is pulled out from the socket 30 with the pressing part 26b being pushed towards the plug main body 20a, whereby the plug 20 can be easily withdrawn from the socket 30. This means that the plug 20 and socket 30 can be stably connected, and the operations to attach and detach the plug 20 and socket 30 can be simplified.

Furthermore, the inventive plug and connecting structure for an endoscope provided therewith are not limited to the mode of embodiment described above, and suitable modifications may be made. For example, in the mode of embodiment described above, the endoscope is a device which is inserted into a patient's stomach or intestines etc. to observe the inside of the stomach or intestines, but the endoscope used with the inventive plug and connecting structure for an endoscope provided with said plug is not limited to observation of the stomach and intestines, and it may be used for other applications.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A plug for attaching to a base end of an endoscope and connecting to a socket, said socket being provided on a main body side of an endoscope device, said plug comprising:
    an image guide comprising an image guide fiber and an image guide rod, said image guide rod being generally aligned with a base end of said image guide fiber;
    a light guide comprising a light guide fiber and a light guide rod, said light guide rod being generally aligned with a base end of said light guide fiber; and
    a plug main body for fixing the base end of the image guide fiber and the base end of the light guide fiber in a parallel state, the base end of the image guide fiber and the base end of the light guide fiber being separated by a space;
    in combination with the socket, the plug being connected to the socket to form a connecting structure, the socket comprising a first hole including a fitting portion for receiving the image guide and a position-aligning portion for regulating positioning of the image guide, the socket further comprising a second hole including a fitting portion for receiving the light guide and a position-aligning portion for regulating positioning of the light guide;
    wherein the plug further comprises an elastic engaging piece, said elastic engaging piece having a base end comprising an engaging part linked to a base end of the plug main body, said elastic engaging piece further having a tip end comprising a pressing part of smaller width than a width of the engaging part, wherein the engaging part is formed so as to be separable from the plug main body, wherein the socket further comprises an engaging wall part having a hole to be engaged, said hole to be engaged comprising a wide hole having a width allowing for insertion of the engaging part and further comprising a narrow hole connected to the wide hole and having a width allowing insertion of the pressing part, wherein when the plug is fitted into the socket, the engaging part is pressed at an edge of the wide hole so as to be urged towards the plug main body, and wherein when the engaging part passes through the wide hole, it moves away from the plug main body so that the pressing part is positioned inside the narrow hole and the engaging part engages with an edge of the abovementioned narrow hole.

2. The plug of claim 1, wherein the plug main body comprises a rod fixing part for fixing the image guide rod and the light guide rod, and further comprises a fiber housing part for housing the image guide fiber and the light guide fiber.

3. The plug of claim 1, wherein an outer diameter of the light guide rod is different from an outer diameter of the image guide rod.

4. The connecting structure of claim 1, wherein a difference between an outer diameter of the image guide rod and an inner diameter of the position-aligning portion of the first hole is not equal to a difference between an outer diameter of the light guide rod and an inner diameter of the position-aligning portion of the second hole.

5. The connecting structure of claim 1, wherein the fitting portion of the first hole tapers toward the position-aligning portion of the first hole from a first diameter to a second diameter, said first diameter of the fitting portion of the first hole being larger than the inner diameter of the position-aligning portion of the first hole, said second diameter of the fitting portion of the first hole being equal to the inner diameter of the position-aligning portion of the first hole, and wherein the fitting portion of the second hole tapers toward the position-aligning portion of the second hole from a third diameter to a fourth diameter, said third diameter of the fitting portion of the second hole being larger than the inner diameter of the position-aligning portion of the second hole, said fourth diameter equal to the inner diameter of the position-aligning portion of the second hole.

6. The connecting structure of claim 1, wherein the outer diameter of the light guide rod is greater than the outer diameter of the image guide rod.

7. The connecting structure of claim 6, wherein the outer diameter of the light guide rod is about 2.13 mm and the outer diameter of the image guide rod is about 2.00 mm.

8. A plug for attaching to a base end of an endoscope in combination with a socket for attachment on a main body side of an endoscope device, said plug comprising:
    an image guide comprising an image guide fiber and an image guide rod, said image guide rod being generally aligned with a base end of said image guide fiber;
    a light guide comprising a light guide fiber and a light guide rod, said light guide rod being generally aligned with a base end of said light guide fiber; and
    a plug main body for fixing the base end of the image guide fiber and the base end of the light guide fiber in a parallel state, the base end of the image guide fiber and the base end of the light guide fiber being separated by a space;
    the socket comprising a first hole including a fitting portion for receiving the image guide and a position-aligning portion for regulating positioning of the image guide, the socket further comprising a second hole including a fitting portion for receiving the light guide and a position-aligning portion for regulating positioning of the light guide;
    a difference between an outer diameter of the image guide rod and an inner diameter of the position-aligning portion of the first hole being unequal to a difference between an outer diameter of the light guide rod and an inner diameter of the position-aligning portion of the second hole.

9. The plug in combination with the socket of claim 8 wherein the difference between the outer diameter of the image guide rod and the inner diameter of the position-aligning portion of the first hole is smaller than the difference between the outer diameter of the light guide rod and the inner diameter of the position-aligning portion of the second hole.

10. The plug in combination with the socket of claim 9 wherein the difference between the outer diameter of the image guide rod and the inner diameter of the position-aligning portion of the first hole is about 0.03 mm, and the difference between the outer diameter of the light guide rod and the inner diameter of the position-aligning portion of the second hole is about 0.27 mm.

* * * * *